United States Patent [19]

Eggensperger et al.

[11] 3,946,006

[45] Mar. 23, 1976

[54] TETRAHYDROTHIADIAZINETHIONES

[75] Inventors: Heinz Eggensperger, Hamburg; Karl-Heinz Diehl, Norderstedt, both of Germany

[73] Assignee: Sterling Drug Inc., New York, N.Y.

[22] Filed: Mar. 5, 1975

[21] Appl. No.: 555,440

[30] Foreign Application Priority Data

Mar. 6, 1974 Germany............................ 2410558

[52] U.S. Cl.............................. 260/243 R; 424/246
[51] Int. Cl.²....................................... C07D 285/34
[58] Field of Search ................................ 260/243 R

[56] References Cited

UNITED STATES PATENTS

| 3,398,146 | 8/1968 | Schorr et al. | 260/243 R |
| 3,475,422 | 10/1969 | Traber | 260/243 R |

*Primary Examiner*—John M. Ford
*Attorney, Agent, or Firm*—Frederik W. Stonner; B. Woodrow Wyatt

[57] ABSTRACT

The invention relates to novel tetrahydro-2H-1,3,5-thiadiazine-2-thiones substituted at the 3 and 5 positions by R—O—A or R—O—benzyl, wherein R is alkyl and A is alkylene, having antimicrobial activity.

8 Claims, No Drawings

TETRAHYDROTHIADIAZINETHIONES

BACKGROUND OF THE INVENTION

1. Field of the Invention

The invention relates to novel tetrahydro-2H-1,3,5-thiadiazine-2-thiones having antimicrobial activity.

2. Description of the Prior Art

Tetrahydro-2H-thiadiazine-2-thiones, substituted at the 3- and 5-positions by methyl, ethyl, propyl, butyl, phenyl, phenethyl, benzyl, etc., having antimicrobial properties, have been described in the literature [A. Rieche et al., Arch. Pharm. 293, 957–967 (1960); A. Rieche et al., Arch. Pharm. 296, 770–784 (1963)]. However, these known compounds do not possess a balanced ratio of lipoid and water solubility which is prerequisite for optimal activity and industrial utility.

SUMMARY OF THE INVENTION

In a composition of matter aspect of the invention there are provided novel 3,5-bis-(R—O—A)-tetrahydro-2H-1,3,5-thiadiazine-2-thiones having the formula

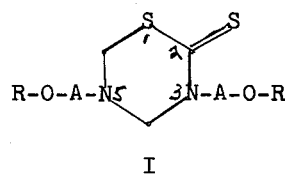

I wherein A is alkylene having from 2 to 6 carbon atoms; and R is alkyl having from 1 to 3 carbon atoms.

In a second composition of matter aspect of the invention there are provided 3,5-bis-(R—O—benzyl)-tetrahydro-2H-1,3,5-thiadiazine-2-thiones having the formula

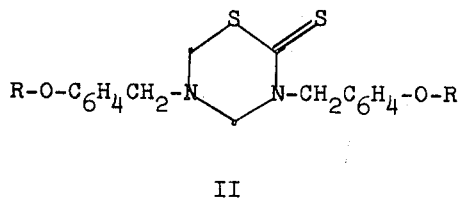

II wherein R is alkyl having from 1 to 3 carbon atoms.

The compounds of formulas I and II are useful as antimicrobial agents.

DETAILED DESCRIPTION INCLUSIVE OF THE PREFERRED EMBODIMENTS

The compounds of formulas I and II are prepared by initially reacting two moles of an alkoxyalkylamine of the formula R—O—A—$NH_2$ or an alkoxybenzylamine of the formula R—O—$C_6H_4CH_2NH_2$ with carbon disulfide followed by reaction with two moles of formaldehyde (as paraformaldehyde). The product is then isolated and purified using standard procedures. The reaction is carried out in a suitable solvent, inert to the conditions of the reaction, e.g., an alkanol such as ethanol. During the initial reaction of the amine with carbon disulfide, the reaction temperature is maintained at about 20° to 30° C. and, after addition of the paraformaldehyde, the reaction temperature is maintained at about 50° to 60° C. The time required for the initial reaction is about 30 minutes, and for the complete reaction about one and one-half to two hours.

The alkoxyalkylamines and alkoxybenzylamines belong to a class of known compounds and are readily available or may be readily prepared by well known procedures.

As used in this specification the term alkylene, as represented by A in formula I, means a group containing from two to six carbon atoms having its two free valence bonds on different carbon atoms, for example —$CH_2CH_2$—, —$CH(CH_3)CH_2$—, —$CH_2CH(CH_3)$—, —$C(CH_3)_2CH_2$—, —$CH_2CH_2CH_2$—, —$CH_2CH(CH_2CH_3)$—, —$CH_2CH(CH_2CH_2CH_3)$—, and —$CH_2CH_2CH_2CH_2CH_2CH_2$—; and the term alkyl, as represented by R in formulas I and II, means methyl, ethyl, propyl, and isopropyl.

In the compounds of formula II, the alkoxy substituent, represented by R—O, may occur at the 2,3, or 4 position of the benzyl radical.

A preferred species of formula I is the compound wherein A is alkylene having from 2 to 3 carbon atoms; and particularly preferred is the compound wherein R is methyl.

A preferred species of formula II is the compound wherein R is methyl.

The compounds of formulas I and II generally are obtained as clear oils and have excellent solubility in polar solvents and excellent lipoid solubility. For example, the compounds of the invention are infinitely soluble in triethylene glycol, butyl diglycol, 1,2,-propylene glycol and polyglycol 400. The compounds of the invention also have amost infinite solubility in nonpolar solvents such as benzene, toluene, xylene, carbon tetrachloride and chloroform.

The compounds of formulas I and II possess useful antimicrobial activity, thus indicating the use of these compounds as antimicrobial agents. As used in this specification the term antimicrobial means antibacterial and antifungal.

The compounds of formulas I and II can be utilized for disinfecting and/or preserving aqueous solutions and dispersions, emulsions, such as aqueous coating compositions and cutting oil emulsions, and inanimate surfaces. In utilizing the compounds of formulas I and II, they can be formulated by preparing a dilute solution in an aqueous medium or a solution, containing if desired a surfactant, conventional carriers and/or adjuvants, or alternatively in an organic medium in which the compounds are soluble. In utilizing the compounds of the invention for preserving aqueous solutions, dispersions or emulsions, they can be added to such liquids in effective preserving and disinfecting amounts without formulation or formulated as described hereinbefore. In utilizing the hereinbefore described formulations for disinfecting surfaces, they can be applied by conventional means such as spraying, swabbing and immersion. For this purpose, the compounds of the invention can be formulated as aerosol sprays and foams.

The bacteriological effectiveness of the compounds of the invention was determined with reference to minimal inhibiting concentrations, that is, the minimal concentration that will effect complete inhibition of germ growth (MIC). The test procedure is as follows:

A 1% suspension, botained by homogenizing 500 mg. of the test agent in 50 ml. of 0.5% natrosol solution (natrosol 250 HRPS = hydroxymethylcellulose), is serially diluted with 0.5% natrosol solution to provide suspensions, in sterile test tubes, having concentrations of 0.1, 0.05, 0.01 and 0.005 percent. To ensure accuracy in dilution, the suspensions are mixed with the aid of a mechanical mixer. The dilutions (6 ml.) are added to sterile cups and immediately 10 filter discs ($\phi$ about 10 mm) are placed on the surface of the liquid in each cup. The filter discs, which slowly sink to the bottom on becoming saturated, are left in the solutions for one hour. 16-Hour old cultures of *Escherichia coli, Staphylococcus aureus, Pyoceanus fluorescens* and *Proteus vulgaris* are diluted at the ratio of 1:10 in glucose broth. 1-Week cultures of *Penicillium glaucum, Aspergillus niger, Chaetomium globosum, Trichoderma viride, Humicola sp., Scopulariopsis brevicaulis, Pullularia pullulans, Sclerophoma pityophila, Saccharomyces cerevisiae* and *Candida albicans* are harvested by rinsing and diluted 1:10 in nutrient broth.

Standard II nutrient agar plates, with an addition of lactose and bromothymol blue (BROLAC agar) for bacteria, and Sabouraud agar plates for yeasts and fungi, are dried and labeled (10 Sabouraud agar plates and 4 nutrient agar plates were used per preparation). Of the diluted germ suspensions, 0.05 ml (1 drop) is inoculated onto each plate. Prior to further treatment, the plates are allowed to stand for one-half hour to absorb the germ suspension. Filter discs, corresponding to each of the five dilutions, are placed on the surface of each inoculated plate for each culture (step 1). The plates are examined for zones of inhibition after twenty-four hours incubation in the case of bacteria, and after three days incubation in the case of yeasts and fungi. Antimicrobial activity is indicated by occurance of a zone of inhibition. In the case of bacteria, the purity of the culture can be determined at the same time by lactose fermentation as indicated by color change in the nutrient medium. A visible inhibition ring is designated as negative growth an no inhibition ring as 3+ growth. If a test agent exhibits good growth inhibition associated with good capacity for diffusion, it can occur that that test agent, at the highest concentration tested, inhibits the growth on the entire surface of the nutrient medium, and therefore the MIC cannot be ascertained from that particular test. A new dilution series then is prepared, with only one, or at most two, filter discs being placed on the surface of each plate for each culture. Activity is then determined as described above.

The MIC values, expressed in percent concentration of the test agent, is presented in TAble 1 for compounds of the invention having formula I designated Example 1 (R—O—A = $CH_2CH_2OCH_3$), Example 2 (R—O—A = $CH_2CH_2OCH_3$) and Example 4(R—O—A = $CH_2CH_2CH_2\ OCH_3$), and for two known compounds, designated A (3,5-dibenzyl-tetrahydro-2H-1,3,5-thiadiazine-2-thione) and B[3,5-bis(2-hydroxyethyl)-2H-1,3,5-thiadiazine-2-thione].

Table 1

| | MIC Valves (% conc.) | | | | |
|---|---|---|---|---|---|
| | | | Compound | | |
| Microorganism | A | B | Ex. 1 | Ex. 2 | Ex. 4 |
| S. aureus | 1 | 0.05 | 0.05 | 0.07 | 0.05 |
| E. coli | 1 | 1 | 0.1 | 0.1 | 0.1 |
| P. fluorescens | 1 | 0.1 | 0.1 | 0.1 | 0.1 |
| P. vulgaris | 1 | 1 | 0.1 | 0.1 | 0.05 |
| P. glaucum | >1 | 1 | 0.005 | 0.05 | <0.003 |
| A. niger | >1 | 1 | 0.03 | 0.1 | <0.003 |
| C. globosum | >1 | 1 | 0.005 | 0.01 | |
| T. viride | >1 | 1 | 0.03 | 0.1 | |
| Humicola sp. | >1 | 0.1 | 0.01 | <0.005 | |

Table 1-continued

| | MIC Valves (% conc.) | | | | |
|---|---|---|---|---|---|
| | | | Compound | | |
| Microorganism | A | B | Ex. 1 | Ex. 2 | Ex. 4 |
| S. brevicaulis | >1 | 0.1 | 0.005 | <0.005 | |
| P. pullulans | >1 | 0.01 | 0.005 | 0.05 | <0.003 |
| S. pityophila | >1 | 0.01 | 0.005 | <0.005 | <0.003 |
| S. cerevisiae | >1 | 0.1 | 0.05 | 0.01 | <0.003 |
| C. albicans | >1 | 1 | 0.05 | 0.05 | 0.01 |

The invention is illustrated by the following examples without, however, being limited thereto.

EXAMPLE 1

3,5-Bis(3-methoxypropyl)-tetrahydro-2H-1,3,5-thiadiazine-2-thione 35.6 g (0.4 mole) 3-methoxypropylamine in 200 ml ethanol, was treated dropwise, with stirring and cooling, with 15.2 g (0.2 mole) carbon disulfide, the temperature being maintained at about 20°–25°C. After the addition was completed, stirring was continued for about an additional thirty minutes at room temperature. 12.5 g (0.4 mole) paraformaldehyde was then added and stirring was continued for another two hours at 50°–55°C. The reaction solution was concentrated under reduced pressure and the residue obtained was filtered, to give 53.5 g of the title compound as a clear yellow oil. (Yield: 97% of theory). Anal. Calcd for $C_{11}H_{22}N_2O_2S_2$: N, 10.06; S, 23.03. Found: N, 10.31; S, 22.90.

EXAMPLE 2

3,5-Bis(2-methoxyethyl)-tetrahydro-2H-1,3,5-thiadiazine-2-thione 30 g (0.4 mole) 2-methoxyethylamine in 200 ml ethanol was treated dropwise, with stirring and cooling, with 15.2 g (0.2 mole) carbon disulfide. Stirring was continued for 20 minutes and then 12.5 g (0.4 mole) paraformaldehyde was added and stirring was continued an additional one hour at 50°–55°C. The reaction solution was concentrated under reduced pressure to give the title compound as a light yellow, lightly viscous liquid. (Yield: 93% of theory). Anal. Calcd for $C_9H_{18}N_2O_2S_2$: N, 11.2; S, 25.6. Found: N, 10.6; S, 25.2.

EXAMPLE 3

3,5-Bis(4-methoxybenzyl)-tetrahydro-2H-1,3,5-thiadazine-2-thione 54.8 g (0.4 mole) 4-methoxybenzylamine in 100 ml ethanol was treated dropwise, with stirring and cooling, with 15.2 g (0.2 mole) carbon disulfide while the temperature was maintained at about 20°–25°C. After completion of the addition, stirring was continued for about thirty minutes, while the temperature was allowed to rise to 30°C. 12.5 g (0.4 mole) paraformaldehyde then was added and stirring was continued for two hours at 50°–55°C. resulting in a clear solution. After two days, the reaction product crystallized from the reaction mixture, and was collected by filtration and recrystallized from ethanol to give 26.8 g of the title compound as a white crystalline product; m.p. 118°–119°C; (Yield 37% of theory). Anal. Calcd for $C_{19}H_{22}N_2O_2S_2$: N, 7.5; S, 17.1 Found: N, 7.4; S, 16.6.

EXAMPLE 4

3,5-Bis(3-ethoxypropyl)-tetrahydro-2H-1,3,5-thiadiazine-2-thione 41.2 g (0.4 mole) 4-ethoxypropylamine in 100 ml ethanol was treated dropwise, with stirring and cooling, with 15.2 g carbon disulfide, the temperature being maintained at about 20° to 25°C. After completion of the addition, stirring was continued for about thirty minutes at room temperature. 12.5 g (0.4 mole) paraformaldehyde was then added and stirring was continued for two hours at 50° to 60°C. The reaction solution was concentrated and the residue filtered to give the title compound as a clear yellow oil. Anal. calcd for $C_{13}H_{26}N_2O_2S_2$: N, 9.1; S, 20.9. Found: N, 9.2; S, 21.4.

We claim:

1. 3,5-Bis(R—O—A)-tetrahydro-2H-1,3,5-thiadiazine-2-thione having the formula

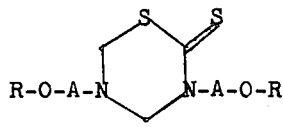

wherein A is alkylene having from 2 to 6 carbon atoms; and R is alkyl having from 1 to 3 carbon atoms.

2. 3,5-Bis(R—O—A)-tetrahydro-2H-1,3,5-thiadiazine-2-thione according to claim 1 wherein A is alkylene having from 2 to 3 carbon atoms.

3. 3,5-Bis(R—O—A)-tetrahydro-2H-1,3,5-thiadiazine-2-thione according to claim 2 wherein R is alkyl having from 1 to 2 carbon atoms.

4. 3,5-Bis(3-methoxypropyl)-tetrahydro-2H-1,3,5-thiadiazine-2-thione according to claim 3.

5. 3,5-Bis(2-methoxyethyl)-tetrahydro-2H-1,3,5-thiadiazine-2-thione according to claim 3.

6. 3,5-Bis(3-ethoxypropyl)-tetrahydro-2H-1,3,5-thiadiazine-2-thione according to claim 3.

7. 3,5-Bis(R—O—benzyl)-tetrahydro-2H-1,3,5-thiadiazine-2-thione having the formula

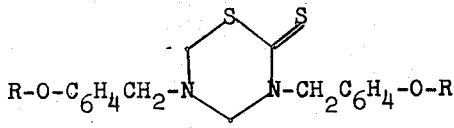

wherein R is alkyl having from 1 to 3 carbon atoms.

8. 3,5-Bis(4-methoxybenzyl)-tetrahydro-2H-1,3,5-thiadiazine-2-thione according to claim 7.

* * * * *